United States Patent [19]

Heine et al.

[11] Patent Number: 5,223,863
[45] Date of Patent: Jun. 29, 1993

[54] BINOCULAR OPHTHALMOSCOPE WITH TILTING MIRROR

[75] Inventors: Helmut A. Heine; Otto H. Schmidt, both of Herrsching; Helmut Rosenbusch, Welthelm, all of Fed. Rep. of Germany

[73] Assignees: Propper Mfg. Co., Inc., Long Island City, N.Y.; Heine Optotecnik GmbH & Co., KG, Herrsching, Fed. Rep. of Germany

[21] Appl. No.: 637,733

[22] Filed: Jan. 7, 1991

[30] Foreign Application Priority Data

Jun. 12, 1989 [DE] Fed. Rep. of Germany ... 3919181C1

[51] Int. Cl.⁵ .................................. A61B 3/10
[52] U.S. Cl. ...................... 351/205; 351/214
[58] Field of Search ............ 351/205, 214, 216, 221; 359/375, 377

[56] References Cited

U.S. PATENT DOCUMENTS

| | | | |
|---|---|---|---|
| 4,449,797 | 5/1984 | Kocher et al. | 351/205 |
| 4,681,413 | 7/1987 | Schmidt et al. | 351/205 |
| 4,684,227 | 8/1987 | Schmidt et al. | 351/205 |
| 4,710,002 | 12/1987 | Pomerantzeff et al. | 351/205 |
| 4,807,987 | 2/1989 | Barnstable et al. | 351/205 |

Primary Examiner—Rodney B. Bovernick
Attorney, Agent, or Firm—Aufrichtig Stein & Aufrichtig

[57] ABSTRACT

A binocular stereoscopic viewing device for examining an eye having a light source and a first light guide for directing light from the light source to the eye to be illuminated. A second light guide redirects light representing the stereoscopic image of the eye. A support mechanism supports both the first light guide and second light guide and is operable for moving in directions towards and away from the eye. A tilting mechanism repositions the first light guide relative to the second light guide for varying the angle at which light from the light source is directed by the first light guide toward the eye to be illuminated.

45 Claims, 4 Drawing Sheets

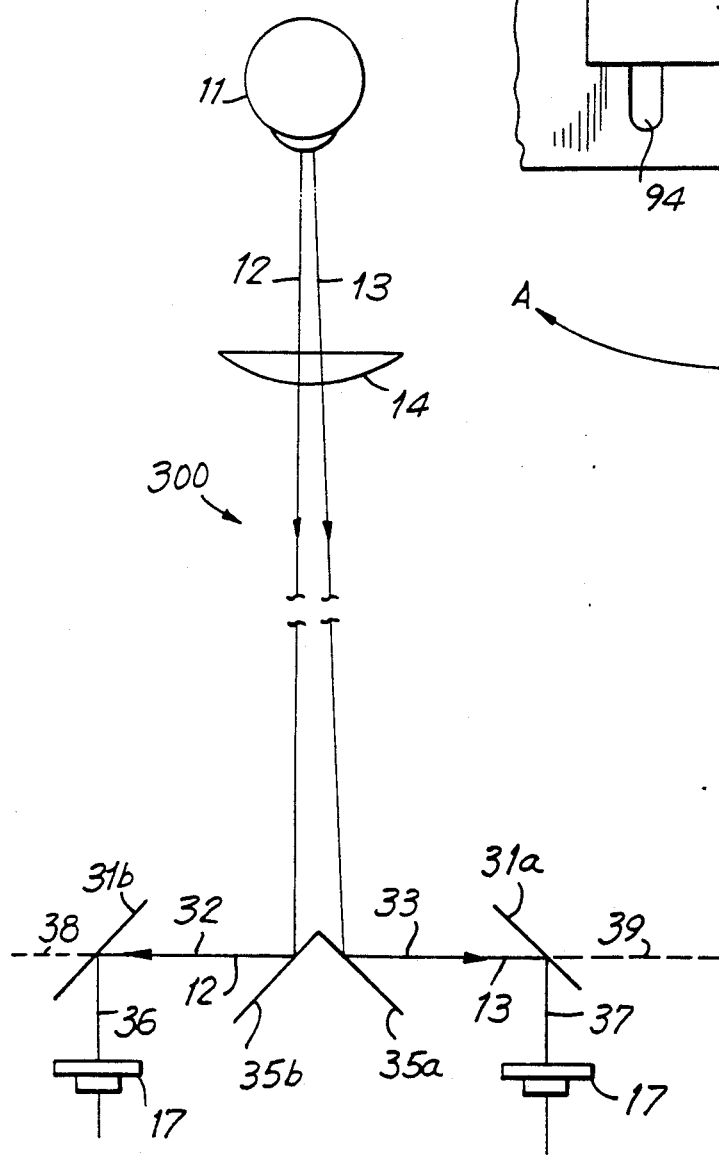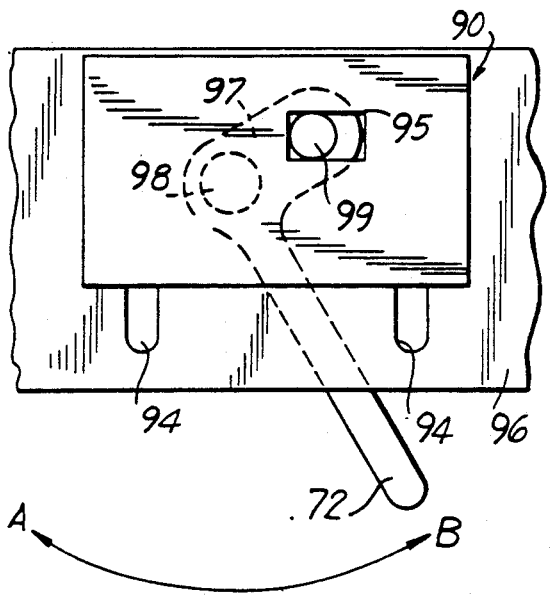

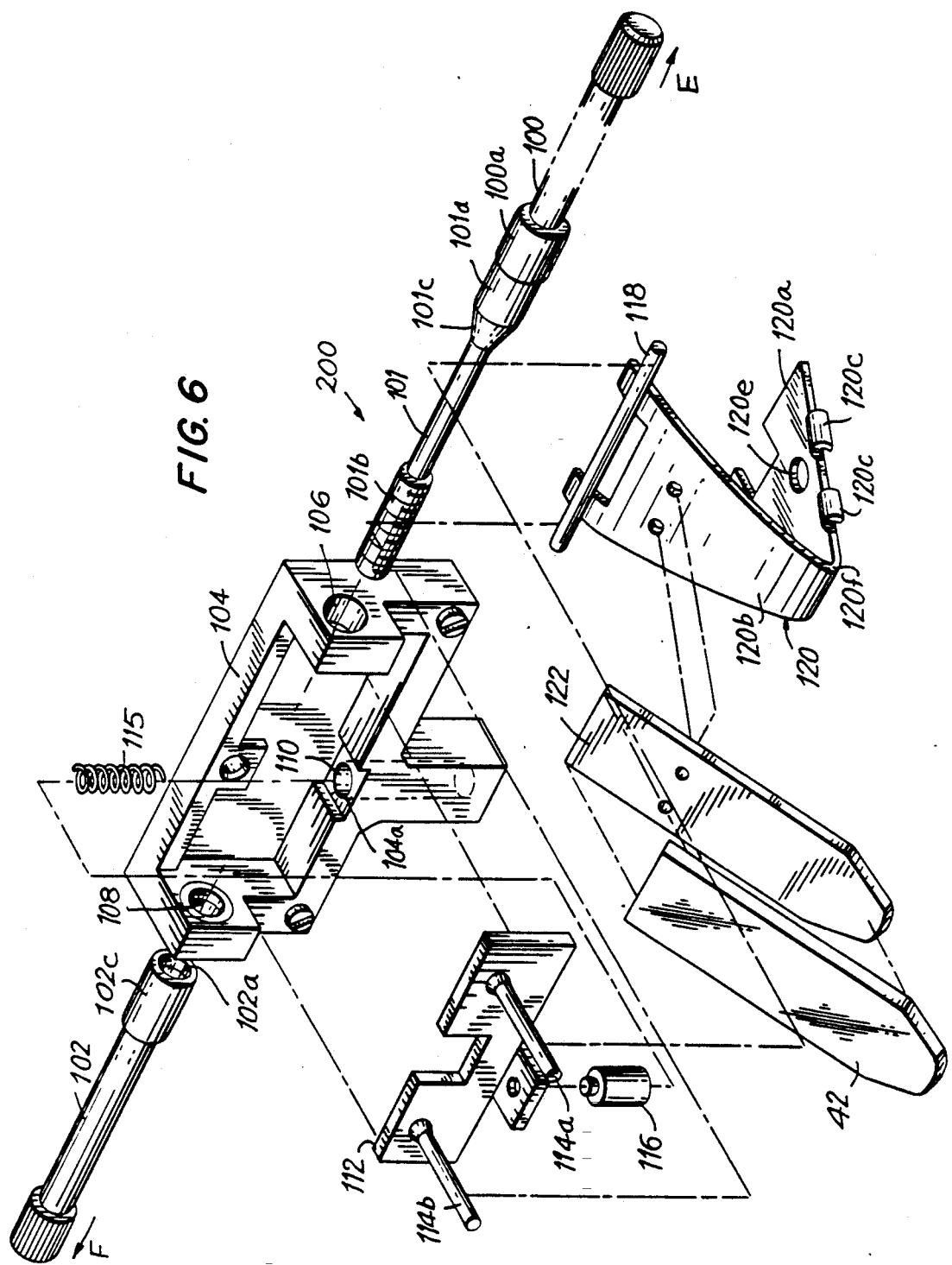

BINOCULAR OPHTHALMOSCOPE WITH TILTING MIRROR

BACKGROUND OF THE INVENTION

This invention relates generally to a binocular stereoscopic viewing device, and in particular, to a binocular ophthalmoscope having a tilting mirror for directing light from a source of light toward the eye of a patient for stereoscopic observation of the latter.

A binocular ophthalmoscopic for indirect observations of a patient's eye includes an illumination unit connected to an observation unit. The observation unit deflects two observation beams and represents the optical path for observing the patient's eye. The illumination beam provided by the illumination unit represents the optical path for illuminating the patient's eye. The illumination and observation beams are directed from the ophthalmoscope to the eye of the patient. For optimum stereopsis, the two observation beams must be separated from each other as far as possible while falling within the pupil of the eye to be examined. The illumination beam, which must also strike the pupil of each eye to be examined, should be separated as far as possible from the images of the examiner's pupils.

Preferably, the illumination beam and two observation beams are separated as far as possible from each other within each eye to be examined by dilating each pupil to be examined through the application of a drug. Dilation of a patient's eye at times may not be possible or practical.

A first type of conventional binocular indirect ophthalmoscope (BIO), such as disclosed in U.S. Pat. No. 4,684,227, adjusts the observation and illumination beams for stereoscopic viewing by mounting on a common platform two mirrors for reflecting the two observation beams and a third mirror for reflecting the illumination beam. The platform is moved towards or away from the patient's eye in positioning the three beams within the patient's retina.

The BIO of U.S. Pat. No. 4,684,227 is well suited for observing portions of the patient's eye which are substantially at or near the center of the eye. When peripheral portions of the retina are to be examined such as, but not limited to, the upper portion of the retina, positioning of the three beams within the patient's eye is difficult to achieve.

More particularly, a vertical disparity exists between the plane formed by the two observation beams and illumination beam as the three beams enter the pupil of the eye. Based on the portion of the eye to be observed, the distance separating the plane formed by the two observation beams and illumination beam must be varied to ensure that the three beams fit within the pupil of the eye. The maximum vertical disparity is greatest when the portion of the eye to be observed is at the center of the pupil since the shape of the pupil based on the angle at which the three beams enter the pupil is substantially circular. The maximum vertical disparity is least when the portion of the eye to be observed is at the periphery of the retina since the shape of the pupil based on the angle at which the three beams enter the pupil is substantially elliptical (i.e., the maximum vertical disparity is highly compressed).

The maximum vertical disparity is varied in the BIO U.S. Pat. No. 4,684,227 by moving the platform which supports the mirrors for reflecting the observation and illumination beams. It is difficult, however, to sufficiently reduce the maximum vertical disparity so that all three beams fit within the pupil when the peripheral portion of the eye is to be examined.

In a second type of conventional BIO, such as disclosed U.S. Pat. No 4,449,797, two mirrors are arranged on a wedge-shaped platform which can be moved towards or away from the patient's eye to adjust the position at which the observation beams enter the eye. The mirror associated with the illumination beam for adjusting the position at which the illumination beam enters the pupil is not located on the wedge-shaped platform. To adjust the position at which the observation beam enters the pupil the mirror associated with the illumination beam is rotated. In other words, similar to the BIO of U.S. Pat. No. 4,684,227, for adjusting vertical disparity, the BIO of U.S. Pat. No. 4,449,797 provides only one control for adjusting the position at which the illumination beam enters the pupil. It is therefore difficult to adjust vertical disparity with the degree of precision demanded when observing peripheral portions of the eye.

Accordingly, it is desirable to provide an improved binocular ophthalmoscope for indirect observation of an eye which has a greater range of vertical disparities as compared to a conventional binocular indirect ophthalmoscope. A higher degree of precision in vertical disparity adjustment should also be provided by the binocular ophthalmoscope.

SUMMARY OF THE INVENTION

Generally speaking, in accordance with the invention, a binocular stereoscopic viewing device for examining an eye includes a light source for producing light and a first light guide for directing the light from the light source toward the eye to be illuminated. The device also includes a second light guide for redirecting light representing the stereoscopic image of the eye. A platform for supporting the first light guide and the second light guide is moveable in directions towards and away from the eye. The device further includes a tilting mechanism for repositioning the first light guide relative to the second light for varying the angle at which light from the light source is directed by the first light guide towards the eye to be illuminated.

The desired vertical disparity is provided by moving the platform in combination with repositioning of the tilting mechanism. In particular, the illumination beam can be adjusted by moving the platform which supports the first light guide and/or repositioning the tilting mechanism of the first light guide. Accordingly, the device provides a greater range of vertical disparities and a higher degree of precision in vertical disparity adjustment as compared to a conventional binocular indirect ophthalmoscope.

In a first feature of the invention the tilting mechanism includes a rotatable bar for movement in linear reciprocating directions, a bracket mechanism responsive to the bar for moving in linear reciprocating directions perpendicular to the linear reciprocating directions of the bar and a spring-like member responsive to movement by the bracket mechanism for pivoting the first light guide about a fixed point relative to the second light guide. The rotatable bar further includes a cam surface. The bracket mechanism includes at least one pin for moving along the cam surface as the bar travels in linear reciprocating directions. Preferably, the cam surface has a frusto-conical shape. Each pin of the bracket mechanism extends towards the first light guide. The bracket mechanism also includes a spring which biases the bracket mechanism in a direction toward the bar.

The spring-like member includes two resilient arms integrally connected at the fixed point. One of the arms is fixedly secured to the tilting mechanism. The first light guide is fixedly secured to the other of the two arms. Preferably the first light guide includes a first mirror and the second light guide includes second and third mirrors.

In another aspect of the invention, a method for binocular stereoscopic observation of an eye includes the steps of generating light from a light source and reflecting light from the light source toward the eye to illuminate the latter. The light is reflected by the first light guide. The method also includes the steps of reflecting light representing the stereoscopic image of the eye by a second light guide and moving a support mechanism relative to the eye. The support mechanism supports the first light guide and second light guide. The method further includes the step of repositioning the first light guide relative to the second light guide for varying the angle at which light from the light source is directed by the first light guide towards the eye.

Similar to the binocular stereoscopic viewing device, the method for binocular stereoscopic observation of an eye provides a greater range of vertical disparities and a higher degree of precision in vertical disparity adjustment as compared to a conventional binocular indirect ophthalmoscope.

Accordingly, it is an object of the invention to provide an improved binocular indirect ophthalmoscope which has a greater range of vertical disparities as compared to a conventional binocular indirect ophthalmoscope.

It is another object of the invention to provide an improved binocular indirect ophthalmoscope which more precisely adjusts the vertical disparity as compared to a conventional binocular indirect ophthalmoscope.

Still other objects and advantages of the invention will, in part, be obvious and will, in part, be apparent from the specification.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a schematic diagram of a binocular ophthalmoscope in accordance with the invention;

FIG. 5 is a bottom plan view of the binocular ophthalmoscope; and

FIG. 6 is an exploded view of that portion of the binocular ophthalmoscope associated with the tilting mirror.

DESCRIPTION OF THE PREFERRED EMBODIMENT

Figure 2:
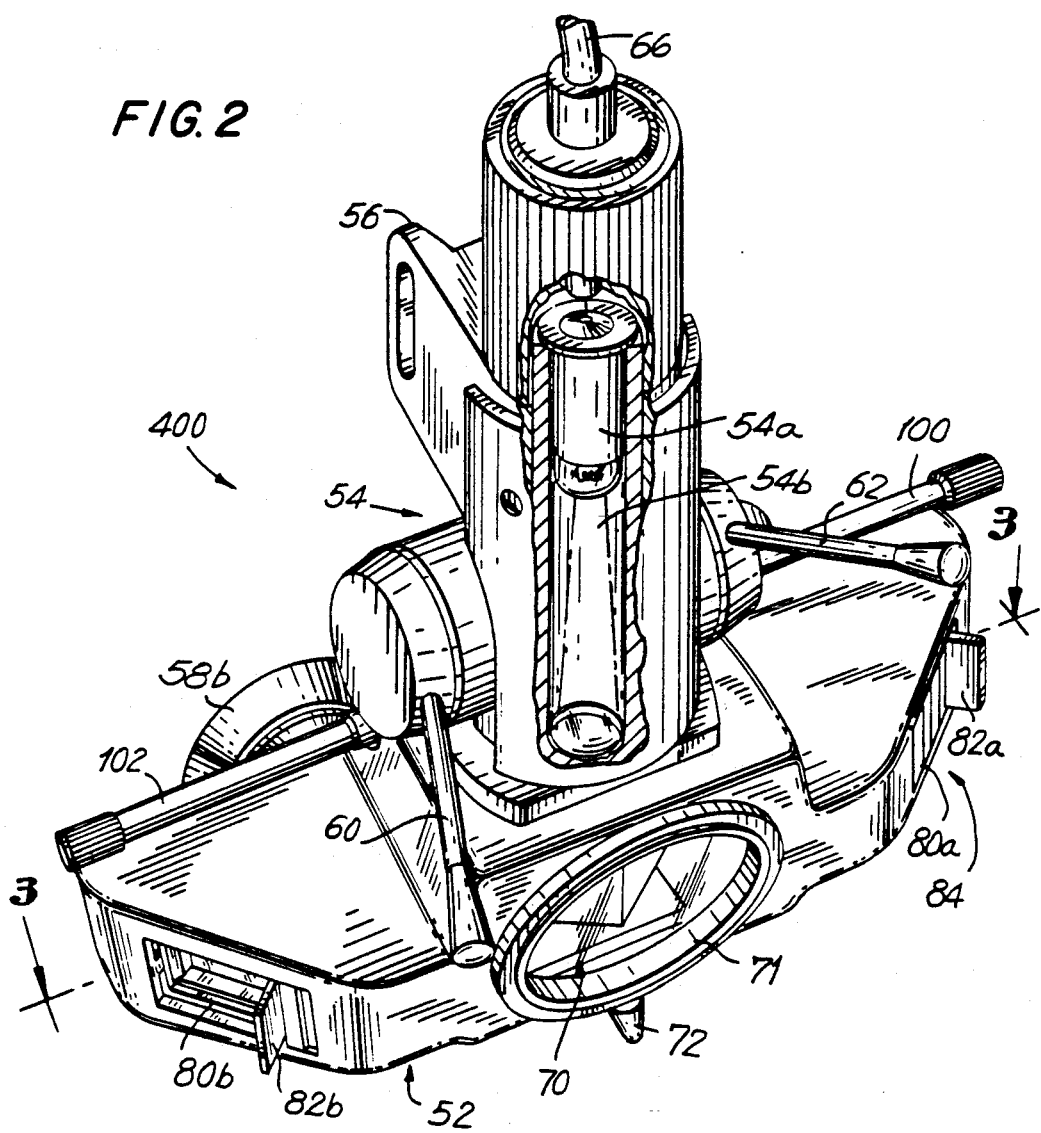
FIG. 2 is a perspective view of a binocular ophthalmoscope in accordance with the invention.
Figure 3:
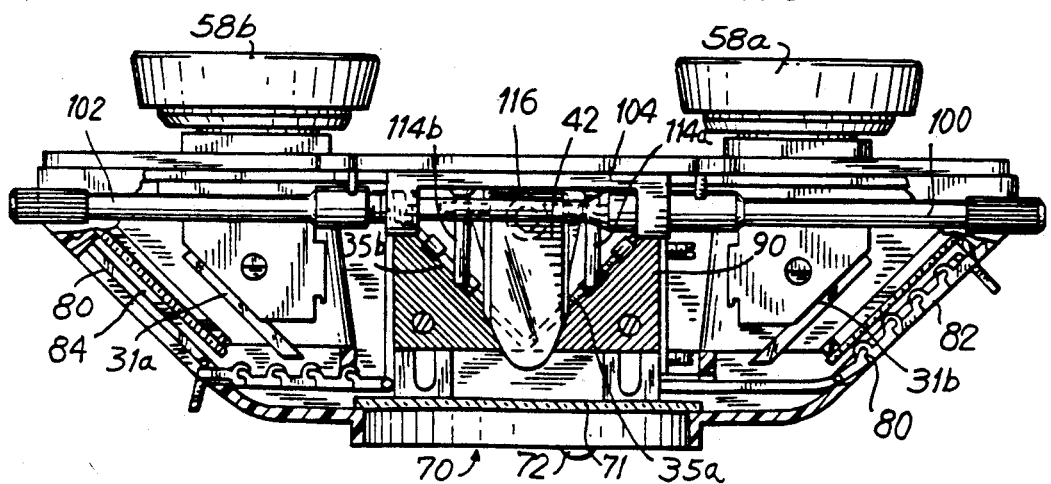
FIG. 3 is a sectional view taken along lines 3—3 of FIG. 2.

Referring now to FIG. 1, a binocular ophthalmoscope, generally indicated at 300, and constructed in accordance with the internal structure of the preferred embodiment of the invention includes a pair of internal mirrors 35a and 35b for reflecting a pair of light rays 12 and 13, which are redirected by an ophthalmoscopic lens 14 and represent the image from a portion (e.g. the fundus) of an eye 11. Light rays 12 and 13 are observation beams and represent the optical path for observing eye 11.

A pair of image splitters 31a and 31b receive the images reflected by internal mirrors 35a and 35b, respectively. Internal mirrors 35a and 35b redirect light rays 13 and 12 so as to travel in the same plane, but in opposite directions along a pair of optical observation paths 33 and 32, respectively.

Light rays 12 and 13 are further divided by image splitters 31a and 31b, respectively. Image splitter 31a creates a pair of optical observation paths 37 and 39 along which light ray 13 travels. Image splitter 31b creates a pair of optical observation paths 36 and 38 along which light ray 12 travels. Light rays 12 and 13 travel along optical observation paths 36 and 37, respectively, and then through a pair of oculars 17 to the examiner's eye (not shown), to create a binocular stereoscopic vision of eye 11. At the same time, light rays 12 and 13 travel along optical observation paths 38 and 39, respectively, in creating a monocular non-stereoscopic image of eye 11.

The stereoscopic and non-stereoscopic image of eye 11 are produced by ophthalmoscope 300 without interference from other light sources. Further, by reducing the number of light guides required, ophthalmoscope 300 provides an image of eye 11 less distorted than provided in a conventional binocular ophthalmoscope. Loss of light from patient's eye 11 can be further reduced by replacing image splitters 31a and 31b with external mirrors when third party viewing is not required.

Figure 4:
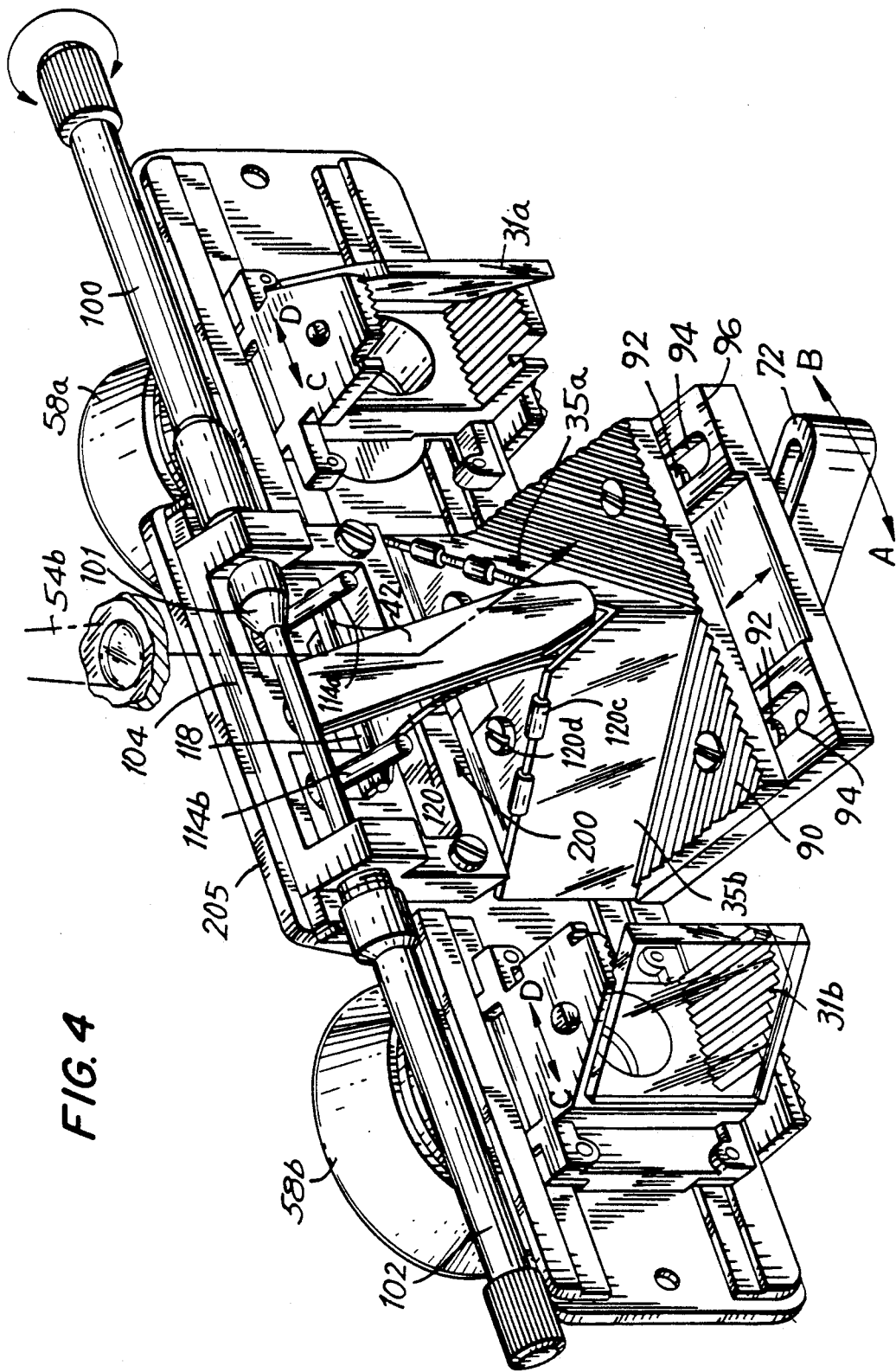
FIG. 4 is a perspective view of the binocular ophthalmoscope observation unit including the tilting mirror of FIG. 3.

FIGS. 2-6 illustrate a binocular ophthalmoscope 400 in accordance with the invention incorporating the light guide array of FIG. 1. Many of the elements and construction of binocular ophthalmoscope 400 are similar to the binocular ophthalmoscope disclosed in U.S. Pat. No. 4,684,227 which is incorporated herein by reference thereto Binocular ophthalmoscope 400 includes an illumination unit 54 and an observation unit 52 rigidly connected thereto. A bracket 56 is secured to illumination unit 54 and can be used to fasten binocular ophthalmoscope 400 to a headband (not shown), or to a spectacle frame (not shown). Adjustable eyepieces 58a and 58b are secured to illumination unit 54 through which a user (examiner) observes pupil 11 of a patient. Eyepieces 58a and 58b can be moved in directions denoted by a pair of arrows C and D, as shown in FIG. 4, to adjust for the interpupillary distance of the observer. Levers 60 and 62 of FIG. 2 can be used to couple luminous-field diaphragms and filters into the path of illumination from illumination unit 54 to the patient. Illumination unit 54 includes a halogen lamp light source 54a which is supplied with current through a cable 66. In an alternative embodiment, fiber optic illumination may be provided by means of an external light source and a fiber optics cable. Light source 54a produces an illumination beam 54b which, as explained below, is directed toward eye 11 to illuminate the latter.

An optical aperture or window 70 through which light passes between the patient and the observer is closed by a plain glass disk 71 to prevent the intrusion of dust into observation unit 52. A single lever 72, which is centrally located relative to observation unit 52 and equally accessible to both left-handed and right-handed users, can be used to simultaneously set the position of the images of the examiner's pupil (i.e., the observation beams) and the position of the image of the light source (i.e., the illumination beam) in pupil 11 of the patient, i.e., convergence and parallax.

A pair of windows 80a and 80b are provided in a pair of side portions 84 of binocular ophthalmoscope 400 to allow third parties to view the image represented by light rays 12 and 13, respectively. Windows 80a and 80b are each provided with a sliding door 82 to open and close the associated window.

In operation, the path of illumination beam 54b from light source 54a within illumination unit 54 passes through (not shown) a condensing lens and a diaphragm (not shown) which is adjustable by lever 60. Optical filters within illumination unit 54 can be placed in and removed from the illumination path by means of lever 62. An objective lens produces an image of the diaphragm at a defined distance in front of ophthalmoscope 400. A more detailed discussion of the illumination path is disclosed in U.S. Pat. No. 4,684,227 which has been incorporated herein by reference thereto.

As shown in FIG. 4, illumination beam 54b is reflected by a tilting mirror 42 through aperture 70 towards eye 11 of the patient. Tilting mirror 42 is supported on a mirror carrier 90 towards and away from eye 11. By moving mirror carrier 90, the vertical disparity between the plane defined by the two observation beams (i.e., light rays 12 and 13) and the illumination beam 54a can be varied as desired.

The directions of light rays 12 and 13 are redirected by internal mirrors 35b and 35a such that light rays 12 and 13 travel in the same plane, but in opposite directions with respect to one and another along optical observation paths 32 and 33, respectively. The paths along which light rays 12 and 13 travel are further divided by image splitters 31b and 31a as discussed above.

Light rays 12 and 13 travel through image splitters 31b and 31a and then along optical observation paths 38 and 39 before passing through windows 80a and 80b, respectively. When doors 82 of windows 80a and 80b are open, third party viewers may view the non-stereoscopic view of eye 11. A binocular view of the stereoscopic image of eye 11 is provided through oculars 17.

Referring now to FIGS. 4 and 5, mirrors 35a and 35b and tilting mirror 42 are mounted to mirror carrier 90. Mirror carrier 90 slidably rests on a plate 96 forming the interior bottom of the housing of observation unit 52. Mirror carrier 90 includes two rail shaped projections 92 which are disposed in and slidably engaged by two slot-shaped recesses 94 formed in plate 96 which together serve as a carriage-like guideway. Recesses 94 extend parallel to the observation plane and parallel to the axis of aperture 70 so that mirror carrier 90 is displaceably moved towards and away from aperture 70. Lever 72 is pivotally mounted to plate 96 through a pivot rotatably mounted to plate 96. The pivot includes a shaft 98 projecting through an opening in plate 96 outwardly from the bottom of observation unit 52, an arm 97 extending at an angle with lever 72 parallel to the bottom of observation unit 52 and a recess of plate 96 in a cam guide 99 received in a cam recess 95 in the bottom of mirror carrier 90. Lever 72 is secured to projecting shaft 98 so that the pivoting of lever 72 rotates shaft 98. Accordingly, cam guide 99 moves mirror carrier 90 as cam guide 99 slides in cam recess 95. Lever 72 pivots in the directions of arrows A and B, and thereby displaces mirror carrier 90 along slot-shaped recesses 94 towards and away from aperture 70, respectively.

Referring now to FIGS. 4 and 6, observation unit 52 further includes a mechanism 200 for controlling the angle of inclination of tilting mirror 42. The angle of inclination of tilting mirror 42 can be adjusted by mechanism 200 independently of or in combination with movement of mirror carrier 90 to change the vertical disparity between illumination on beam 54b andthe pair of observation beams (i.e., light rays 12 and 13). More specifically, tilting mirror 42 redirects illumination beam 54b so as to change the point at which illumination beam 54b enters the pupil of eye 11. By providing both mirror carrier 90, for moving tilting mirror 42 towards and away from eye 11 and mechanism 200 for controlling the angle of inclination of tilting mirror 42, a wide range of vertical disparities and precise adjustment of the vertical disparity is achieved. A stereoscopic image of eye 11 including peripheral portions such as, but not limited to, the upper retina can be observed.

Mechanism 200 includes rotatable bar-like members 100 and 102. Members 100 and 102 are integrally connected to one another through a bar-like member 101. Member 101 has a bullet-shaped first end 101a and a threaded second end 101b. First end 101a is connected to bar-like member 100 in any well known manner and includes a frusto-conical surface 101c. Second end 101b is threaded into an opening 102a of member 102 to connect member 101 to member 102. A support bracket 104 includes openings 106 and 108 through which first end 101a and second end 101b extend. Support bracket 104 is disposed within observation unit 52 of binocular ophthalmoscope 400 against an outer wall 205. Opening 108 has internal threads which mate with threaded second end 101b.

Bar member 102 includes a proximal end 102c which has a larger outer diameter than the diameter of opening 108. Consequently, proximal end 102c serves as a stop for moving members 100, 101 and 102 in a direction denoted by an arrow E. Similarly, member 100 has a proximal end 100a which is dimensioned to have a larger outer diameter than the diameter of opening 106. Proximal end 100a serves as a stop for moving members 100, 101 and 102 in a direction denoted by an arrow F. By rotating members 100 and 102 clockwise and counterclockwise, the threading interaction between second end 101b of member 101 and the internal threads of opening 108 results in bar-like members 100, 101 and 102 moving in linear reciprocating directions.

Surface 101c serves as a cam surface for engagement with a support bar/pin 114a Support bar 114a is connected to a support backing 112 which is coupled to support member 104. Support member 104 also includes an opening 104a for receiving and holding a spring 115 inserted into an opening 110. Resting on top of spring 115 within opening 101a is a cylindrical member 116. Spring 115 presses against cylindrical member 116, which pushes support backing 112 upwardly toward member 101. Consequently, support bar 114a is biased against surface 101c.

As members 100 and 102 are turned, cam surface 101c engages support bar 114a so as to move support backing 112 upwardly or downwardly in linear reciprocating directions which are perpendicular to the linear reciprocating directions traveled by members 100, 101 and 102. Support bars 114a and 114b are in continuous contact with a cross bar 118. A resilient spring-like member 120 which includes a pair of arms 120a and 120b is connected to cross bar 118 and provides the bias for continuous contact with support bars 114a and 114b. A connection tab 122 is connected to arm 120b in any well known suitable manner. Arm 120a includes fingers 120c which rest on mirrors 35a and 35b. A pair of screws 120d (shown in FIG. 4) extend through a pair of openings 120e of arm 120a (shown in FIG. 6) and are suitably secured to fixedly position member 120 relative to mirror carrier 90.

Tilting mirror 42 is connected to connection tab 122 through adhesive or in any other well known manner. Accordingly, tilting mirror 42, connection tab 122 and support member 120 form a single unit. As support bars 114a and 114b move upwardly or downwardly in constant engagement with cross bar 118, tilting mirror 42 pivots about a fixed point 120f relative to mirrors 35a and 35b to vary the inclination of tilting mirror 42. Support member 120 in this preferred embodiment of the invention has resilient arms 120a and 120b to allow tilting mirror 42 to pivot. Alternatively, a single flat, rigid member forming support member 120 can be coupled to a pivot to control the movement of tilting mirror 42.

As now can be readily appreciated, in accordance with the invention, the illumination beam 54b can be adjusted by moving mirror carrier 90 and/or rotating members 100 and 102. Greater precision in adjusting for vertical disparity and a greater range of vertical disparities are provided as compared to a conventional binocular indirect ophthalmoscope.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A binocular stereoscopic viewing device for examining an eye, comprising
   light source means for producing light;
   first light guide means for directing the light from said light source means in a direction toward the eye to illuminate the latter;
   second light guide means for redirecting light representing the stereoscopic image of the eye;
   support means for supporting said first light guide means and said second light guide means, said support means being movable in directions towards and away from said eye so as to reposition said first light guide means and said second light guide means in directions towards and away from said eye; and
   tilting means for repositioning said first light guide means relative to said second light guide means for varying the angle at which the light from said light source means is directed by said first light guide means toward the eye to illuminate the latter.

2. The binocular stereoscopic viewing device of claim 1, wherein said tilting device includes first means operable for movement in at least a first direction, second means responsive to said first means for movement in second and third directions and third means responsive to said second means for pivoting said first light guide means about a fixed point relative to said second light guide means.

3. The binocular stereoscopic viewing device of claim 2, wherein said first means includes a cam surface and said second means includes cam means, said cam means for moving along said cam surface as said first means travels in at least said first direction.

4. The binocular stereoscopic viewing device of claim 3, wherein said first means is rotatable and moves in said first direction in response to being rotated.

5. The binocular stereoscopic viewing device of claim 4, wherein said second means further includes bracket means for supporting said cam means.

6. The binocular stereoscopic viewing device of claim 5, wherein said second direction and said third direction are opposite to one another and wherein said second means also includes bias means for biasing said bracket means in said third direction.

7. The binocular stereoscopic viewing device of claim 3, wherein said first and second directions are substantially perpendicular to each other.

8. The binocular stereoscopic viewing device of claim 7, wherein said second means further includes bracket means for supporting said cam means.

9. The binocular stereoscopic viewing device of claim 8, wherein said second direction and said third direction are opposite to one another and wherein said second means also includes bias means for biasing said bracket means in said third direction.

10. The binocular stereoscopic viewing device of claim 3, wherein said second means further includes bracket means for supporting said cam means.

11. The binocular stereoscopic viewing device of claim 10, wherein said second direction and said third direction are opposite to one another and wherein said second means also includes bias means for biasing said bracket means in said third direction.

12. The binocular stereoscopic viewing device of claim 2, wherein said first means is rotatable and moves in said first direction in response to being rotated.

13. The binocular stereoscopic viewing device of claim 12, wherein said first and second directions are substantially perpendicular to each other.

14. The binocular stereoscopic viewing device of claim 2, wherein said first and second directions are substantially perpendicular to each other.

15. The binocular stereoscopic viewing device of claim 2, wherein said first means is operable for movement in linear reciprocating directions.

16. The binocular stereoscopic viewing device of claim 1, wherein said first light guide means includes a first mirror and wherein said second light guide means includes second and third mirrors.

17. A binocular stereoscopic viewing device for examining an eye, comprising
light source means for producing light;
first light guide means for directing the light from said light source means toward the eye to illuminate the latter;
second light guide means for redirecting light representing the stereoscopic image of the eye;
support means for supporting said first light guide means and said second light guide means, said support means being movable in directions towards and away from said eye;
tilting means for repositioning said first light guide means relative to said second light guide means for varying the angle at which the light from said light source means is directed by said first light guide means toward the eye to illuminate the latter;
said tilting means including first means operable for movement in at least a first direction, second means responsive to said first means for movement in second and third directions and third means responsive to said second means for pivoting said first light guide means about a fixed point relative to said second light guide means; and
said first means including a cam surface having a frusto-conical shape and said second means including cam means, said cam means for moving along said cam surface as said first means travels in at least said first direction.

18. The binocular stereoscopic viewing device of claim 17, wherein said cam means includes at least one pin extending toward said first light guide means.

19. The binocular stereoscopic viewing device of claim 18, wherein said first means is rotatable and moves in said first direction in response to being rotated.

20. The binocular stereoscopic viewing device of claim 18, wherein said third means includes spring means having two resilient arms integrally connected at said fixed point, one of said arms fixedly secured to said tilting means and wherein said first light guide means is fixedly secured to the other of said arms.

21. The binocular stereoscopic viewing device of claim 17, wherein said second means further includes bracket means for supporting said cam means.

22. The binocular stereoscopic viewing device of claim 21, wherein said second direction and said third direction are opposite to one another and wherein said second means also includes bias means for biasing said bracket means in said third direction.

23. A binocular stereoscopic viewing device for examining an eye, comprising
light source means for producing light;
first light guide for directing the light from said light source means toward the eye to illuminate the latter;
second light guide means for redirecting light representing the stereoscopic image of the eye;
support means for supporting said first light guide means and said second light guide means, said support means being movable in directions towards and away from said eye;
tilting means for repositioning said first light guide means relative to said second light guide means for varying the angle at which the light from said light source means is directed by said first light guide means toward the eye to illuminate the latter;
said tilting means including first means operable for movement in at least a first direction, second means responsive to said first means for movement in second and third directions and third means responsive to said second means for pivoting said first light guide means about a fixed point relative to said second light guide means;
said first means including a cam surface and said second means including cam means, said cam means for moving along said cam surface as said first means travels in at least said first direction; and
said cam means including at least one pin extending toward said first light guide means.

24. The binocular stereoscopic viewing device of claim 23, wherein said first means is rotatable and moves in said first direction in response to being rotated.

25. The binocular stereoscopic viewing device of claim 24, wherein said first and second directions are substantially perpendicular to each other.

26. The binocular stereoscopic viewing device of claim 24, wherein said second means further includes bracket means for supporting said cam means.

27. The binocular stereoscopic viewing device of claim 26, wherein said second direction and said third direction are opposite to one another and wherein said second means also includes bias means for biasing said bracket means in said third direction.

28. The binocular stereoscopic viewing device of claim 27, wherein said third means includes spring means having two resilient arms integrally connected at said fixed point, one of said arms fixedly secured to said tilting means and wherein said first light guide means is fixedly secured to the other of said arms.

29. The binocular stereoscopic viewing device of claim 24, wherein said third means includes spring means having two resilient arms integrally connected at said fixed point, one of said arms fixedly secured to said tilting means and wherein said first light guide means is fixedly secured to the other of said arms.

30. The binocular stereoscopic viewing device of claim 23, wherein said first and second directions are substantially perpendicular to each other.

31. The binocular stereoscopic viewing device of claim 30, wherein said second means further includes bracket means for supporting said cam means.

32. The binocular stereoscopic viewing device of claim 31, wherein said second direction and said third direction are opposite to one another and wherein said second means also includes bias means for biasing said bracket means in said third direction.

33. The binocular stereoscopic viewing device of claim 23, wherein said second means further includes bracket means for supporting said cam means.

34. The binocular stereoscopic viewing device of claim 33, wherein second direction and said third direction are opposite to one another and wherein said second means also includes bias means for biasing said bracket means in said third direction.

35. The binocular stereoscopic viewing device of claim 34, wherein said third means includes spring means having two resilient arms integrally connected at said fixed point, one of said arms fixedly secured to said tilting means and wherein said first light guide means is fixedly secured to the other of said arms.

36. The binocular stereoscopic viewing device of claim 23, wherein said third means includes spring means having two resilient arms integrally connected at said fixed point, one of said arms fixedly secured to said tilting means and wherein said first light guide means is fixedly secured to the other of said arms.

37. A binocular stereoscopic viewing device for examining an eye, comprising light source means for producing light;

first light guide means for directing the light from said light source means toward the eye to illuminate the latter;

second light guide means for redirecting light representing the stereoscopic image of the eye;

support means for supporting said first light guide means and said second light guide means, said support means being movable in directions towards and away from said eye;

tilting means for repositioning said first light guide means relative to said second light guide means for varying the angle at which the light from said light source means is directed by said first light guide means toward the eye to illuminate the latter;

said tilting means including first means operable for movement in at least a first direction, second means responsive to said first means for movement in second and third directions and third means responsive to said second means for pivoting said first light guide means about a fixed point relative to said second light guide means; and said third means including spring means having two resilient arms integrally connected at said fixed point, one of said arms fixedly secured to said tilting means and wherein said first light guide means is fixedly secured to the other of said arms.

38. A binocular stereoscopic viewing device for examining an eye, comprising light source means for producing light;

first light guide means for directing the light from said light source means toward the eye to illuminate the latter;

second light guide means for redirecting light representing the stereoscopic image of the eye;

support means for supporting said first light guide means and said second light guide means, said support means being movable in directions towards and away from said eye;

tilting means for repositioning said first light guide means relative to said second light guide means for varying the angle at which the light from said light source means is directed by said first light guide means toward the eye to illuminate the latter;

said tilting means including first means operable for movement in at least a first direction, second means responsive to said first means for movement in second and third directions and third means responsive to said second means for pivoting said first light guide means about a fixed point relative to said second light guide;

said first means including a cam surface and said second means including cam means, said cam means for moving along said cam surface as said first means travels in at least said first direction; and said third means including spring means having two resilient arms integrally connected at said fixed point, one of said arms fixedly secured to said tilting means and wherein said first light guide means is fixedly secured to the other of said arms.

39. A binocular stereoscopic viewing device for examining an eye, comprising light source means for producing light;

first light guide means for directing the light from said light source means toward the eye to illuminate the latter;

second light guide means for redirecting light representing the stereoscopic image of the eye;

support means for supporting said first light guide means and said second light guide mans, said support means being movable in directions towards and away from said eye;

tilting means for repositioning said first light guide means relative to said second light guide means for varying the angle at which the light from said light source means is directed by said first light guide means toward the eye to illuminate the latter;

said tilting device includes first means, said first means rotatable for movement in at least a first direction in response to being rotated, second means responsive to said first means for movement in second and third directions and third means responsive to said second means for pivoting said first light guide means about a fixed point relative to said second light guide means; and said third means including spring means having two resilient arms integrally connected at said fixed point, one of said arms fixedly secured to aid tilting means and wherein said first light guide means is fixedly secured to the other of said arms.

40. A method for binocular stereoscopic observation of an eye, comprising the steps of:

generating light from a light source;

reflecting light from the light source toward the eye to illuminate the latter, said light being reflected by first light guide means;

redirecting light representing the stereoscopic image of the eye by second light guide means;

moving said support means towards and away from said eye, said support means supporting said first light guide means and second light guide means; and repositioning the first light guide means relative to said second light guide means for varying the angle at which light from said light source is directed by said first light guide means toward the eye.

41. The method of claim 40, wherein the step of repositioning includes pivoting the first light guide means about a fixed point, relative to said second guide means.

42. The method of claim 40, wherein the step of repositioning includes moving first means in at least a first direction, moving second means in response to movement of said first means in at least a second direction and pivoting said first light guide means about a fixed point relative to said second light guide means in response to movement of said second means.

43. The method of claim 42, further including moving said first means in linear reciprocating directions.

44. The method of claim 43, wherein said first means is moved by rotating said first means.

45. The method of claim 44, further including moving said second means in linear reciprocating directions which are substantially perpendicular to said first direction.

* * * * *